United States Patent [19]

Nelson

[11] 4,208,194

[45] Jun. 17, 1980

[54] MONITORING DEVICE

[75] Inventor: Leigh E. Nelson, Hastings, Minn.

[73] Assignee: Minnesota Mining and Manufacturing Co., Saint Paul, Minn.

[21] Appl. No.: 836,763

[22] Filed: Sep. 26, 1977

[51] Int. Cl.$^2$ .................... B01D 13/00; B01D 53/22; B01D 59/10

[52] U.S. Cl. ........................ 55/158; 55/389; 73/23; 73/29; 55/385 C

[58] Field of Search ............... 55/74, 75, 72, 158, 55/16, 385 C, 387, 71, 389; 210/506, 500 M; 73/23, 29

[56] References Cited

U.S. PATENT DOCUMENTS

| | | | |
|---|---|---|---|
| 2,933,154 | 4/1960 | Lauterbach | 55/97 |
| 3,019,127 | 1/1962 | Czerwonka | 55/316 |
| 3,651,618 | 3/1972 | Klein et al. | 55/16 |
| 3,791,910 | 2/1974 | Bowser | 55/389 |
| 3,911,080 | 10/1975 | Mehl et al. | 55/158 |
| 3,924,219 | 12/1975 | Braun | 73/23 R |
| 3,950,980 | 4/1976 | Braun et al. | 73/23 R |
| 4,040,802 | 8/1977 | Deitz et al. | 55/74 |
| 4,040,805 | 8/1977 | Nelms et al. | 55/158 |

FOREIGN PATENT DOCUMENTS

| | | | |
|---|---|---|---|
| 2256843 | 6/1974 | Fed. Rep. of Germany | 55/316 |
| 2079460 | 12/1971 | France | 55/16 |

*Primary Examiner*—Frank Sever
*Attorney, Agent, or Firm*—Cruzan Alexander; Donald M. Sell; Carolyn A. Bates

[57] ABSTRACT

An improved device for measuring the amount of a selected component of a fluid mixture wherein the particulate sorbent material which collects the selected component is immobilized in a matrix of polytetrafluoroethylene.

7 Claims, No Drawings

MONITORING DEVICE

This invention relates to an improved device for analyzing the amount of a selected component in a fluid mixture. More particularly it relates to an improved personal monitor for determining the level of human exposure to harmful vapors and gases in ambient air.

Personal monitors of the type described herein are known and disclosed in U.S. Pat. Nos. 3,924,219 and 3,950,980. These monitors may be attached to clothing in close proximity to the breathing zone of the wearer. Generally, these monitors comprise body members forming a shallow chamber having an open end. Inside the chamber is disposed a collecting layer which collects the preselected component from the air. Across the open end of the chamber and spaced from the collecting layer are one or more porous attenuating layers to prevent impingement of moving air on the collecting layer and allow the selected components to reach the collecting layer by diffusion.

The collecting substances useful in these monitors include materials which adsorb, absorb, react with or otherwise generally combine with the selected components being measured. In some cases the collecting substance is particulate in nature such as activated charcoal, alumina or silica. When particulate collecting materials are used, certain problems have been encountered. Firstly, particulate material tends to shift position inside the monitor as the monitor is moved about. If the exposed surface of the collecting material is not smooth, uncertain concentration gradients may develop and the accuracy of subsequent measurements may be compromised. Secondly, when it is necessary to transfer the collecting material to a separate vial for analysis of the collected gases, some of the particulate material may be lost or incompletely removed from the monitor thereby introducing additional error into the measurements.

Thus, the need existed for a convenient means of immobilizing or entrapping the particulate collecting substance in a manner which would not impair its ability to combine with the selected components being monitored and which would not interfere with the subsequent analysis of the collected components.

The present invention effectively fulfills this need by providing a monitor wherein the particulate collecting substance is immobilized in a smooth flexible sheet formed by blending the collecting substance with an aqueous dispersion of polytetrafluoroethylene (PTFE) and subsequent formation of the mixture into a composite sheet.

Composite sheets of PTFE and various filler materials are known. Copending application Ser. No. 827,785, filed Aug. 25, 1977, now U.S. Pat. No. 4,153,661, and assigned to the same assignee as the present application discloses high tensile strength porous PTFE composite sheets containing various fillers including carbon, silica or alumina, and a process for their preparation. The sheet is described as being uniformly porous making it suitable for use as a filtering material, for electrolytic cells, as a gas diffusion membrane and other uses known for PTFE sheets.

Composite sheets formed from PTFE and various filler materials are also disclosed, for example, in the following U.S. Pat. Nos. 2,997,448, 3,010,536, 3,315,020, 3,407,249 and 3,407,096. Although composite sheets comprising PTFE and various filler materials were previously known, it was heretofore unrecognized that certain filler materials contained therein could be utilized to collect selected gaseous components from a gaseous mixture for subsequent analysis. The surprising discovery that particulate collecting material, e.g. activated charcoal, could be immobilized into a PTFE sheet and retain virtually all of its ability to combine with selected gaseous materials and the discovery that sorbed components could be readily desorbed from the sheet form the basis of the present invention.

According to the present invention there is provided an improved device for measuring the amount of at least one selected component in a fluid mixture. The device comprises body members forming a shallow chamber having an open end, a collecting layer disposed within the chamber for combining with the selected component and one or more porous attenuating layers spaced apart from the collecting layer and disposed across the open end of the chamber. The improvement of the present invention resides in the use of a composite sheet of polytetrafluoroethylene and a particulate collecting material as the collecting layer. The PTFE composite sheet provides a collecting layer which is highly efficient in collecting the selected component. It presents a smooth, even collecting surface which does not shift, stratify, channel or otherwise change position when the device is moved. Furthermore, the PTFE is chemically inert and does not interfere with the removal of the selected component from the sheet for subsequent analysis. The particulate collecting material is immobilized in the sheet so that none is lost from the device during use or during transfer from the device for analysis.

Another embodiment of the invention resides in the use of the PTFE composite sheet as an attenuating layer spaced from the detecting layer. In this embodiment, the sheet, which is highly porous, may be used to attenuate the flow of the fluid into the chamber and additionally serves as a selective barrier to remove selected components from the fluid which may adversely affect the analysis. In this embodiment, the collecting layer may be a PTFE composite sheet or it may be another type of collecting layer such as a gold film for monitoring mercury vapor.

The term collecting substance as used herein refers broadly to particulate material which adsorbs, absorbs, reacts with or otherwise combines with a selected component of a fluid mixture to remove the component from the mixture. For purposes of further disclosure the terms "sorbent" and "sorbent material" will be used interchangeably with the term "collecting material."

The composite sheet material utilized in the monitors of the invention is prepared by diluting a PTFE latex with water and adding thereto the particulate sorbent material. The resulting mixture is kneaded to form a homogeneous paste. The paste is subsequently calendered to form a thin sheet material. The sheet is then dried at moderate temperatures, preferably under vacuum, to form a composite which can be utilized as a collecting layer containing negligible contaminants.

The resulting composite sheet material is smooth, flexible and porous, and possesses sufficient tensile strength so that it may be cut, rubbed or handled without significant loss of the sorbent material. In spite of the fact that the sorbent is intricately incorporated into the composite, the sorbent characteristics thereof are not significantly impaired.

The PTFE latex utilized in preparing the sheet material is an aqueous dispersion of negatively charged hydrophobic colloid containing particles in the general size range of 0.05 to 0.5 micrometers. A preferred material is Teflon ® 42 containing 32-35% by weight solids of PTFE resin, which is available from the E. I. DuPont Co. Teflon ® 42 is particularly preferred as a commercial raw material since it contains no wetting agent. Teflon ® 30 or 30B, similar products from E. I. DuPont, may also be used, but the composite sheet formed therefrom require heat treatment at higher temperatures, e.g. 300° C., to remove the wetting agents.

The PTFE may be considered as a binder in the sorbent material and generally comprises from about 5 to 50 percent by weight of the composite sheet, and preferably about 15 to 25 percent by weight. The remainder of the sheet is essentially the sorbent material in the preferred amount of 50 to 95 percent by weight, and most preferably 75 to 85 percent by weight. However, in some instances, a portion of non-sorbent particulate filler may be substituted for sorbent material. For example, up to about 50% of the particulate material may be non-sorbent filler if the monitor is to be limited to a short exposure period and/or for low concentrations of monitored vapors.

The sorbent material is generally a particulate material of relatively fine particle size and high surface area. For example, the preferred activated charcoal utilized typically contains particles less than about 45 micrometers in diameter. (About 75% less than 25 micrometers, 50% less than about 12 micrometers and 5% less than 5 micrometers). Generally, the particles will pass 400 mesh U.S. Screen.

The particulate material utilized for the sorbent material in this composite are well known for their ability to sorb vapors of environmental consequence from an ambient atmosphere. They must be essentially insoluble in water. Activated charcoal, alumina or silica are typical examples of suitable sorbent material. In addition, organic chromatographic substances such as Chromosorb, a copolymer of styrene and divinyl benzene in the form of beads, available from Johns-Manville, may also be used in the composite.

As indicated earlier, a filler may be substituted for some of the sorbent material. The filler may consist of clay, talc, titanium dioxide, calcium carbonate, etc. and the particle size is preferably less than about 45 micrometers.

The PTFE dispersion (generally containing about 35 percent solids) is mixed with sufficient additional water and the particulate material to form a homogeneous paste. The larger the particle size of the sorbent material used, the less water is required to form the paste.

The paste or putty-like mass is then transferred to a calendering device where it is calendered between rolls preferably maintained at about 50° C. to about 100° C. to form the sheet material. Preferably, the calendering rolls are made of a rigid material such as steel. A useful calendering device has a pair of rotatable opposed calendering rolls each of which may be heated and one of which may be adjusted toward the other to reduce the gap or nip between the two. Typically, the gap is adjusted to a setting of about 10 to 20 millimeters for the initial pass of the mass and, as calendering operations progress, the gap is reduced to produce a sheet of porous, flexible, easily handled sheet material. The sheet material formed by passing through the calender rolls may be folded and rotated 90° to improve the strength of the final sheet material. In a preferred mode of calendering, the folding and rotating of the mass is performed after each pass. The thickness of the completed porous composite sorbent material is about 0.1 to 2.0 millimeters, with a preferred thickness of about 0.3 to 0.8 mm.

The resulting calendered sheet is baked, preferably under vacuum, in order to provide a porous, sorbent sheet material with minimal impurities which interfere with subsequent analytical procedure. The heating step is easily carried out in a vacuum oven at 150° to 300° C. for from 0.5 to 5.0 hours, at atmospheric pressure to a vacuum of about 100 Torr. It will be apparent to those skilled in the art that baking at a higher temperature under vacuum will require less time to eliminate contaminants, whereas baking at lower temperatures atmospheric temperature will require longer time. Baking at higher temperatures, e.g. 300° C., for longer than about twenty minutes may cause the sheet to become brittle. It is preferred to use a vacuum with an absolute pressure of about 50-125 Torr at a temperature of 150° C. for about 3.0 hours.

In spite of the fact that the sorbent material is bonded so well that the sheet material has appreciable tensile strength, and can be cut, rubbed or flexed without loss of the sorbent, there is relatively little or no loss of the sorbent characteristic. The surface area of the sorbent remains substantially unchanged despite its incorporation into the PTFE matrix. For example, a sample of carbon having a surface area of 917 m$^2$ per gram incorporated into Teflon ® 42 dispersion on an 80 percent carbon basis had a surface area of 734 m$^2$/g of sheet material. The surface area was determined by nitrogen adsorption.

Samples of Teflon ® dispersion-carbon sheet material were exposed to various organic vapors and the vapors were extracted with $CS_2$ and analyzed by gas chromatography. The data in Table I indicates the recovery of the organic vapor.

TABLE I

| Organic Vapor | % Recovery |
| --- | --- |
| Heptane | 103 |
| Toluene | 97 |
| Chlorobenzene | 94 |
| Benzene | 98 |
| Methylethylketone | 94 |

Monitors using these sorbent sheets as collecting layers can be used to monitor methyl ethyl ketone, benzene, ethanol, heptane, toluene, chlorobenzene, trichloroethylene, sulfur dioxide, chlorine, ammonia, hydrogen sulfide and hydrogen chloride and other materials of environmental consequence. The monitor is exposed to the environment for a predetermined length of time, and is generally positioned near the breathing zone of the wearer when used as a personal monitor. Following the exposure period the collected vapors are desorbed from the collecting layer with an elutant such as carbon disulfide. An aliquot of the elutant containing collected material is analyzed using conventional techniques such as gas chromatography.

Alternatively the sorbent sheets may be spaced from the collecting layer and used to attenuate gas flow into the chamber of the monitor. In this position, the sheet may serve as selective barrier to remove certain selected vapors which may interfere with the analysis and allow the vapors to be analyzed to pass through to the collecting layer. For example, a mercury vapor monitor such as that described in U.S. Pat. No. 3,924,219 utilizes a gold film as the collecting (detecting) layer for the mercury vapor. The presence of chlorine in a sampled environment may interfere with accurate measurement of the amount of mercury vapor. Accordingly, it is desirable to filter out chlorine before it reaches the gold film collecting layer. This can be accomplished by providing a filter comprising a porous PTFE-Zeolite composite sheet in which the zeolite has been reacted with an excess of 10 percent N-phenyldi-isopropanolamine in ethanol following formation of the sheet. The sheet selectively filters chlorine while allowing passage of mercury vapor.

The improved monitors of the invention are further illustrated by the following nonlimiting examples.

EXAMPLE 1

This example illustrates the preparation of PTFE-carbon composite sheets for use in organic vapor monitors. The effect of varying the amount of carbon in the sheet on various physical properties of the sheet was determined.

The following sheets were prepared:

| Sample | Weight of Carbon | Wt. of PTFE Dispersion | Volume of Deionized Water |
| --- | --- | --- | --- |
| 1 | 90 g | 29 g | 180 ml |
| 2 | 70 | 29 | 140 |
| 3 | 50 | 29 | 100 |
| 4 | 40 | 29 | 80 |
| 5 | 30 | 29 | 60 |
| 6 | 20 | 29 | 40 |
| 7 | 10 | 29 | 20 |

The carbon used was Witco Activated Charcoal, Type 965, which had been previously ground and classified to remove residual fine particles and then heat-treated at 600° C. under nitrogen for one hour to remove possible trace organic contaminants. The final particle size was determined to be predominantly between 7 and 31 micrometers. The PTFE used was obtained from the E. I. DuPont Company under the tradename Teflon ® 42 aqueous Teflon ® dispersion, 34.4% solids. In each case, the deionized water was added to the Teflon ® 42 dispersion. The diluted Teflon ® 42 was then added to the carbon. The mixture was stirred and then kneaded by hand to form a homogeneous paste.

The carbon-Teflon ®-water paste was then converted to a self-supporting sheet by milling on a two-roll rubber mill having metal rollers controlled at a temperature of 80° C. The milling procedure was as follows:

1. The gap between the two metal rollers was adjusted to approximately ¼ inch (0.6 cm). The rollers were rotating in opposite directions and arranged such that material introduced into the gap tended to be drawn into the gap and calendered under shear forces.

2. The homogeneous paste was forced between the rollers 20 times. Between each pass the material was folded once and rotated at a 90° angle to the direction of the previous pass.

3. The roll gap was decreased to approximately ⅛ inch (0.3 cm). The material was forced between the rollers, folded, rotated 90° as before for ten passes.

4. The roller gap was then reduced in small steps without further folding or rotating the sheet until the final sheet thickness was achieved.

5. The films were then dried in a vacuum oven at 150° C. for 3 hours at a vacuum with an absolute pressure of 50 Torr. The sheets were all approximately 0.015 inches (0.3 mm) in thickness.

The sheet samples were then cut into circular wafers using a 1-3/16 inch (3.0 cm) cutting die. The wafers were used to conduct performance tests, except for porosity and tensile strength which were determined from the sheet samples themselves. The performance tests conducted are described as follows:

(1) Volume and Density—The wafers were weighed on an analytical balance and the thickness measured with a micrometer. The wafer volume and density were calculated. The weight of carbon in each wafer was calculated by multiplying the wafer weight by the percent carbon dry weight in the formulation.

(2) Adsorption Capacity—The adsorption capacity was tested by placing the wafers in a saturated carbon tetrachloride ($CCl_4$) vapor chamber at room temperature for one hour and determining weight gain. The $CCl_4$ activity was calculated by dividing weight gain by wafer thickness. The weight gain in grams was also divided by the weight in grams of carbon in each wafer.

(3) Porosity—The porosity was measured with a W. & L. E. Gurley Densometer, Model 4200. The recorded value was the time (in seconds) required to pass 10 $cm^3$ of air through a one square inch (6.45 $cm^2$) area of sheet at a differential pressure of 0.03 standard atmospheres.

(4) Elutriation Efficiency—The wafers were placed in individual flat containers with covers. A syringe was used to add 2.0 microliters of methyl ethyl ketone (MEK) to each wafer, the cover snapped on and the sealed containers were allowed to stand overnight. The next day, 1.5 milliliters of carbon disulfide ($CS_2$) added to the containers. After 30 minutes, 2 microliter samples of the liquid were withdrawn and injected into a Hewlett Packard Model 5840A gas chromatograph. Samples of a standard solution of 2.0 microliters MEK in 1.5 milliliters of $CS_2$ were also injected (2 microliters). The elutriation efficiency (percent MEK recovery) was determined by comparison of MEK peak area of the unknowns and the standards.

(5) Tensile Strength—Sheet tensile strength was measured on a TM model Instron using one inch strips, one inch jaw separation and one inch/minute crosshead speed. Units were in pounds per square inch.

The following results were obtained:

| Sample No. | Carbon Wt. % | Wafer Thickness (mils) (mm) | Wafer Weight (g) | Wafer Density (g/$cm^3$) | $CCl_4$ Adsorbed (mg) | $CCl_4$ Activity (mg/mm) | Gurley Porosity (sec) | MEK Recovery (%) | Tensile Strength (psi) (kg/$cm^2$) |
| --- | --- | --- | --- | --- | --- | --- | --- | --- | --- |
| 1 | 90.0 | 15.0 (0.38) | 0.196 | 0.721 | 101.5 | 267 | 1.1 | 97.5 | 68 (4.78) |
| 2 | 87.5 | 15.0 (0.38) | 0.201 | 0.738 | 106.0 | 279 | 2.3 | 100.5 | 134 (9.42) |
| 3 | 83.3 | 15.5 (0.39) | 0.216 | 0.767 | 107.6 | 276 | 3.4 | 101.1 | 192 (13.5) |
| 4 | 80.0 | 13.1 (0.33) | 0.192 | 0.806 | 89.6 | 272 | 4.5 | 98.2 | 270 (19.0) |
| 5 | 75.0 | 15.0 (0.38) | 0.229 | 0.842 | 100.2 | 264 | 5.8 | 96.4 | 245 (17.2) |
| 6 | 66.6 | 14.5 (0.37) | 0.244 | 0.926 | 92.9 | 251 | 11.2 | 101.4 | 390 (27.4) |
| 7 | 50.0 | 15.0 (0.38) | 0.315 | 1.157 | 96.1 | 253 | 61.1 | 103.4 | 942 (66.2) |

These data indicate that higher carbon loading gave higher porosity, lower sheet density and lower tensile strength. Sheet sorption properties remained essentially constant, and all sheets in this experiment were suitable for use in organic vapor monitors. The formulation can be tailored to individual applications.

EXAMPLE 2

This example illustrates the effect of varying the thickness of the PTFE-Sorbent composite sheet.

A homogeneous paste was formed from 40 g Witco Type 965 Activated Charcoal, 29 g Teflon ® 42 aqueous Teflon ® dispersion and 80 milliliters of deionized water. Self-supporting sheets were prepared exactly as described in Example 1, except the final rubber mill roll gap was varied to achieve a range of sheet thicknesses. The samples were tested using procedures described in Example 1.

| Sample No. | Wafer Thickness (mils) (mm) | Wafer Weight (g) | Wafer Density (g/cm³) | CCl₄ Adsorbed (mg) | CCl₄ Activity (mg/mm) | Gurley Porosity (sec) | MEK Recovery (%) |
|---|---|---|---|---|---|---|---|
| 1 | 6.2 (0.16) | 0.090 | 0.803 | 42.2 | 264 | 1.7 | 97.4 |
| 2 | 8.0 (0.20) | 0.119 | 0.823 | 58.8 | 294 | 2.6 | 98.3 |
| 3 | 13.1 (0.33) | 0.192 | 0.806 | 89.6 | 272 | 4.5 | 98.2 |
| 4 | 30.3 (0.77) | 0.415 | 0.755 | 194.5 | 253 | 7.9 | 96.3 |

The above data indicate that only the vapor capacity (CCl₄ Adsorbed) and Gurley Porosity are substantially affected by film thickness. Accordingly, sheet thickness can be used to regulate these properties as desired for the specific intended application.

Examples 3–7 are intended to demonstrate that a variety of sorbent materials can be used in the composite sheets, and that useful sorbent activity is retained in the sheet.

EXAMPLE 3

A sample of Witco Type 965 Activated Charcoal was ground and sieved through 400 mesh screen to give a particle size predominately between 5–25 microns. The charcoal was then heated at 600° C. for one hour. A homogeneous paste of 80 grams carbon, 60 grams aqueous Teflon ® 42 aqueous dispersion (34.4% solids) and 160 grams deionized water was prepared and formed into 0.015 inch (0.38 mm) sheet by repeated passes through a two-roll steel roll rubber mill at 80° C. as described in Example 1. The sheet was then dried in an oven at 150° C. for three hours under water aspirator vacuum (about 50 Torr absolute pressure). A circular, 1-3/16 inch (3.0 cm) diameter wafer was cut from the sheet and weighed. The weight of carbon in the wafer was calculated. An approximately equivalent amount of the ground, sieved and fired parent carbon powder was also weighed. The carbon wafer and carbon powder samples were both placed in a saturated benzene vapor chamber in metal weighing dishes. After three days, the weight gain was recorded for each sample. The sorbent activity was calculated by computing the weight gain per gram of carbon. The activity obtained for the carbon wafer was 0.298 g benzene/g carbon compared with a value of 0.293 g benzene/g carbon for the parent carbon sample. Accordingly, the sorbent activity for the PTFE-carbon sheet was virtually identical to that of the free carbon.

EXAMPLE 4

A sample of Johns-Manville Chromosorb ® 102 (a porous styrene divinylbenzene copolymer having a surface area in the range of 300–400 m²/g) was ground using a mortar and pestle and then sieved through 140 mesh screen. A homogeneous paste was prepared from 5 g Chromosorb ® 102, 3.75 g Teflon ® 42, 7 ml deionized water and 2 ml methanol. The methanol was necessary to promote wetting of the Chromosorb ®. The paste was then calendered as described in Example 1 to give a self-supporting sheet approximately 0.015 inch (0.38 mm) thick and dried at 150° C. for 3 hours in the vacuum oven at an absolute pressure of about 50 Torr. The sorbent activity was determined by comparing weight of benzene adsorbed by the sheet to the parent sorbent material as in Example 3. The absorptive activity of the Chromosorb ® 102/Teflon ® 42 sheet was 0.769 g benzene/g Chromosorb ® 102 compared to an activity of 0.750 g benzene/g Chromosorb ® 102 for parent material.

EXAMPLE 5

A sample of Fisher Silica Gel Grade 42 was ground with mortar and pestle, sieved through 140 mesh screen and converted into a PTFE composite sheet. The formulation contained 20 g sieved silica gel and 15 g Teflon ® 42. No additional water was necessary. The composite sheet was formed as described in Example 1. After drying at 150° C. for three hours in the vacuum oven, the sorbent activity of the film was compared to the parent sorbent material in a saturated ethanol vapor chamber at room temperature. The activity of the Teflon ®—bonded film was 0.204 g ethanol/g silica gel, compared to 0.265 g ethanol/g silica gel for the parent material.

EXAMPLE 6

A sample of Matheson, Coleman and Bell Activated Alumina was ground and sieved as described in Example 5. A homogeneous paste was formed from 20 g activated alumina, 15 g Teflon ® 42 dispersion and 7 milliliters of deionized water. The paste was calendered as described in Example 1, but fewer calendering passes were required to achieve tensile strength suitable for handling. The sheet was dried at 150° C. for 3 hours in a vacuum oven. The sorbent activity of the sheet was compared to that of the parent sorbent in the saturated ethanol vapor chamber. The results were complicated by the fact that both film and parent sorbent readily adsorb moisture from the air during handling. The sorbent activity of the sheet was found to be 0.117 g ethanol/g activated alumina, compared to 0.071 g ethanol/g activated alumina for the parent sorbent. Surprisingly, the sorbent activity of the sheet was greater than that of the parent material.

EXAMPLE 7

This example illustrates the use of sorbent particles of larger particle size to form the PTFE composite sheets.

Eight g of Tenax® GC (60×80 mesh), a 2,6-diphenyl-p-phenylene oxide porous polymer developed by Akzo Research Laboratories, was mixed with 5.9 gm of Teflon® 30. (34% suspesnion of Teflon® microparticles in water stabilized with 4% Triton®×100), and enough extra water to form a homogeneous paste. The paste was then formed into a sheet 0.50 mm thick by repeated passes through a two-roll steel roll rubber mill set at 50° C. The material was calendered from a starting thickness of 0.5 cm to a final thickness of 0.5 mm three times. The film was folded after the first two times and inserted into the rollers at a 90° angle. A self-supporting sheet was obtained.

EXAMPLE 8

This example illustrates a PTFE-carbon composite sheet containing an inert filler.

Sixty g of carbon (particle size 37 to 15 micrometers) were mixed with 20 g of kaolin, an inorganic clay filler, and 20 g of Teflon® 30 solids. Enough water was added to form the solids into a homogeneous paste. The paste was then formed into a sheet 0.5 mm thick by repeated passes through a steel roll rubber mill set at 50° C. The material was rolled from a starting thickness of 0.5 cm to a final thickness of 0.5 mm three times. The sheet was folded after the first two times and inserted into the rollers at a 90° angle. The resulting sheet was dried in a muffle furnace under a nitrogen purge at 300° C. for twenty minutes to remove the water and Triton×100 contained in the Teflon® 30. The resulting sheet was pliable, strong, and free of any shedding.

EXAMPLE 9

This example illustrates a PTFE composite sheet for use as a selective barrier in a mercury monitor to filter out interferring chlorine.

A PTFE-Zeolite composite sheet was prepared by uniformly mixing 40 grams Linde No. 541 molecular sieve, 16.5 grams Teflon® 30 (59.7% solids) and 60 grams deionized water. The resulting homogeneous paste was calendered at 80° C. as in Example 1 to a 0.017 inch (0.43 mm) sheet, and the sheet was air dried at room temperature.

In view of the intended use as a selective barrier, and the corresponding need for good porosity characteristics, the sheet porosity was measured using the Model 4200 Gurley HPS tester. At a differential test pressure of 0.03 standard atmospheres, 16.5 seconds were required to pass 10 cubic centimeters of air through 1.0 square inch (6.45 cm²) of the sample. This favorably compares with 35 Gurley seconds for Celanese Celgard® 2500 and indicates that the porosity of the PTFE-Zeolite composite sheet is acceptable.

Next the sheet was saturated with excess solution of 10% N-phenyldi-isopropanolamine (Isonol) in ethanol and the non-entrained excess solution was stripped away.

After drying, the combined Isonol, Zeolite, Teflon sheet was tested as a chlorine gas filter as follows. Ten parts per million of chlorine gas was circulated in a chamber on one side of the test film. A gold film detecting layer as described in U.S. Pat. No. 3,950,980 was used to determine the time to chlorine breakthrough. The breakthrough time was determined by measuring the change in electrical resistance of the gold film, land was found to be in excess of 90 minutes. This indicates over 15 hours protection at the chlorine Threshold Limit Value of 1 part per million.

Consistent with the need for filtering chlorine while passing mercury vapor, the sheet was next mounted on the outer surface of the 3M Brand Mercury Vapor Monitor No. 3600 just below and adjacent to the standard Celgard barrier film used in the product. The monitor was exposed to 0.1 mg Hg/cubic meter air for 8 hours and the change in resistance of the gold film was 7.3% as compared to 8.9% for standard controls without the selective barrier. This shows the utility of the film as a quantitative chlorine barrier which passes mercury vapor.

EXAMPLE 10

This example illustrates a Melamine-Teflon composite sheet for a selective barrier for filtering chlorine gas and passing mercury vapor.

An Aldrich 99% purity Melamine sheet was prepared by uniformly mixing 30 grams Teflon 42 (34.4% solids) with 40 grams particulate Melamine and 5 grams deionized water. The material was processed as in Example 8 to a 0.017 inch (0.43 mm) sheet.

The Gurley porosity test of Example 1 showed the film porosity to be an acceptable 75 Gurley seconds. The chlorine resistance test of Example 8 showed the sheet blocks chlorine for over 295 minutes. The mercury vapor transmission was shown to be 26% of the standard by the procedure used in Example 8.

What is claimed is:

1. In a device for measuring the amount of at least one selected component in a fluid mixture comprising body members forming a shallow chamber having an open end, a collecting layer disposed within said chamber for collecting said selected component and at least one porous attenuating layer spaced apart from said collecting layer and disposed across the open end of said chamber, the improvement wherein said collecting layer consisting essentially of a porous polytetrafluoroethylene sheet containing an effective amount of a pariculate sorbent of particulate size and distribution sufficient to retain substantially all of said selected component for a time sufficient for quantitative measurement.

2. The device according to claim 1 wherein said polytetrafluoroethylene sheet comprises 5 to 50 percent by weight polytetrafluoroethylene.

3. The device according to claim 2 wherein said polytetrafluoroethylene sheet comprises 50 to 95 percent by weight of said particulate sorbent.

4. The device according to claim 3 wherein said polytetrafluoroethylene sheet comprises 75 to 85 percent by weight of said particulate sorbent.

5. The device according to claim 1 wherein the average particle size of said sorbent is less than 45 micrometers.

6. The device according to claim 1 wherein said sorbent is selected from the group consisting of carbon, alumina and silica.

7. The device according to claim 1 wherein said polytetrafluoroethylene sheet further comprises up to about 50 percent by weight of a non-sorbent filler.

* * * * *